United States Patent [19]
McDonald

[11] Patent Number: 5,824,010
[45] Date of Patent: Oct. 20, 1998

[54] SUTURE NEEDLE GUIDE

[76] Inventor: Garth R. McDonald, 13612 Jarrettsville Pike, Phoenix, Md. 22131

[21] Appl. No.: 652,378

[22] Filed: May 23, 1996

[51] Int. Cl.$^6$ .................................................. A61B 17/00
[52] U.S. Cl. ........................... 606/148; 606/150; 606/153
[58] Field of Search ..................................... 606/150, 153, 606/155, 156, 134, 144, 148

[56] References Cited

U.S. PATENT DOCUMENTS

| | | | |
|---|---|---|---|
| 4,553,543 | 11/1985 | Amarasinghe | 606/153 |
| 4,911,164 | 3/1990 | Roth | 606/148 |
| 5,545,171 | 8/1996 | Sharkey et al. | 606/139 |
| 5,554,162 | 9/1996 | De Lange | 606/153 |

OTHER PUBLICATIONS

Suma et al, Vein Holder for Coronary Bypass Surgery, Ann Thorac Surg 43:109–110, Jan. 1987.
Yokoyama et al, "Simple Arterial Graft Holder for Coronary Artery Bypass Grafting", Ann Thorac Surg 1995:59:533–4.

*Primary Examiner*—Jeffrey A. Schmidt
*Attorney, Agent, or Firm*—Cushman Darby & Cushman Intellectual Property Group of Pillsbury Madison & Sutro LLP

[57] ABSTRACT

A suture needle guide and a method of use therefor. A suture needle guide comprises a needle guide member connected to a manually-graspable handle. The needle guide member is inserted, via an arteriotomy, into the lumen of a host blood vessel. The needle guide member includes a portion which is shaped to guide a suture needle so that anastomosis can be more accurately and easily performed, compared to free-handed suturing.

7 Claims, 5 Drawing Sheets

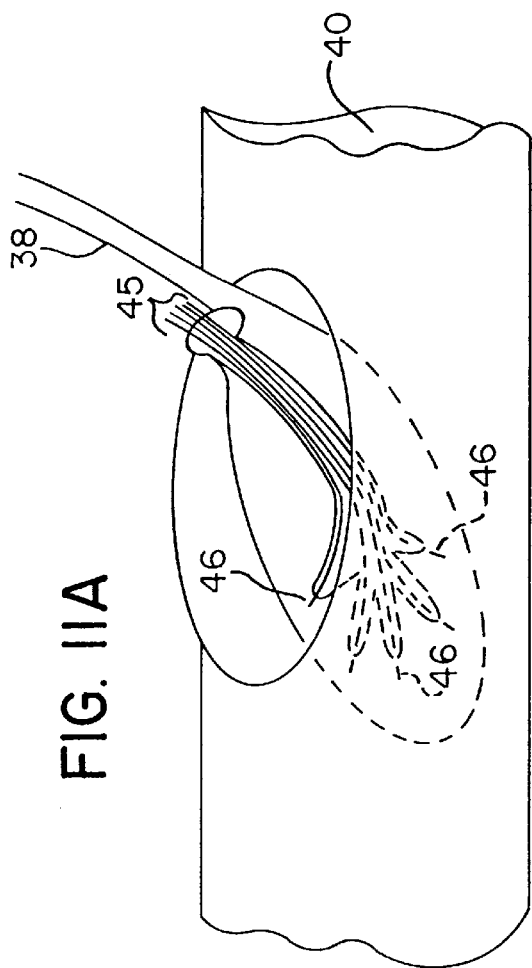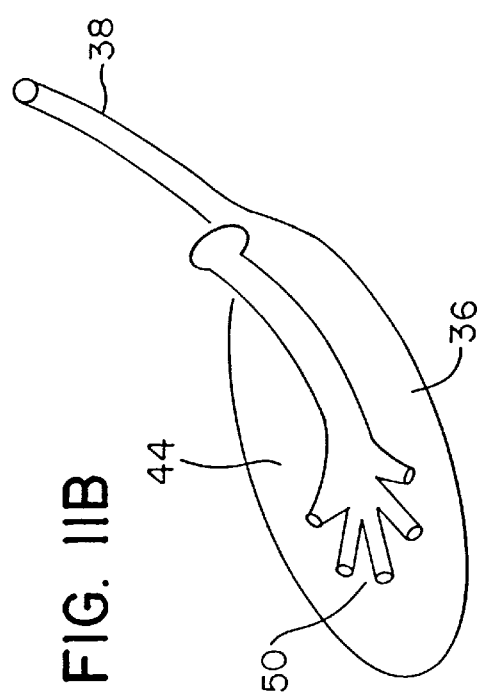

SUTURE NEEDLE GUIDE

FIELD OF THE INVENTION

The present invention relates to a suture needle guide for facilitating accurate placement of sutures, and particularly, to a suture needle guide for facilitating vascular anastomosis, such as in vascular bypass surgery.

BACKGROUND OF THE INVENTION

Vascular end-to-side anastomosis is a common procedure in vascular surgery, comprising attaching a vascular graft end to a host vessel, via an arteriotomy, or opening, formed in the side of the host vessel. This attachment is typically performed by locating a plurality of interrupted or continuous sutures about the periphery of the arteriotomy so as to secure the vascular graft end to the host vessel in communication therewith.

FIG. 1 generally illustrates a host vessel 1 having an arteriotomy 2 formed in a side thereof. Vascular graft segment 3 has an open end 4 of a size suitable for communicating with arteriotomy 2.

FIG. 2 generally illustrates the anastomosis of the host vessel 1 and vascular graft 3. The anastomosis is secured with individual sutures 5 (only four sutures being seen in the side perspective view of FIG. 2).

However, this procedure can be quite difficult due to, for example, limited exposure of the anastomotic site in the surgical field, relatively small and/or delicate vessels, motion in the operative field, impaired or otherwise decreased visibility of the anastomotic site (due to blood seepage in the operative field, for example). These factors make it difficult to accurately place the sutures and raise the possibility of narrowing the anastomosis or otherwise perforating or damaging the host vessel.

It is generally known in the art to use external devices to stabilize the end of the graft vessel to facilitate free-hand placement of sutures.

Suma et al. (*Annals of Thoracic Surgery*, Vol. 43, pp. 109–110, January 1987) disclose two types of vein holders for holding a graft vessel while performing anastomosis. The first type of vein holder according to Suma et al. has a sheath 3 mm in diameter and 15 cm long. The sheath can be partially retracted after insertion into the graft vessel lumen, thereby exposing radially expansible pins. The pins hold open the free end of the vein so that needle placement is more clearly visible to the surgeon.

The second type of vein holder disclosed by Suma et al. has a bullet-shaped end and a hollow body which is introduced into the vessel lumen, again with the effect of holding the free end of the vessel to facilitate needle insertion.

Yokoyama et al. (*Annals of Thoracic Surgery*, Vol. 59, pp. 533–534) disclose an arterial graft holder which can be improvised from a segment of an intravenous catheter. The graft holder, carved from a segment of an intravenous catheter, is inserted into the lumen of the graft, and is manually bent and held with the fingers, having the effect of exposing the free end of the graft.

However, in the devices disclosed by Suma et al. and Yokoyama et al., the sutures are still placed free-handedly. This means that inaccurate placement of sutures, inadvertent puncture of the opposite side of the graft, etc. are still possible.

SUMMARY OF THE INVENTION

It is therefore an objective of the present invention to provide a suture needle guide which facilitates accurate placement of sutures while performing vascular anastomosis. More specifically, it is an objective of the present invention to provide a suture needle guide which is structured to define a specific path of motion for a suture needle in the process of placing a suture.

It is a further objective of the present invention to provide a suture needle guide which helps prevent damage to areas of a host vessel near the anastomotic site.

It is a still further objective to provide a method for performing an end-to-side anastomosis in which sutures are accurately and easily placed.

The guide, according to the present invention, is particularly characterized in that the suture needle or needles are actively guided in forming a suture, as opposed to free-handed placement of sutures, as in the prior art.

The suture needle guide according to the present invention generally comprises a needle guide member connected to a manually-grasped handle. The needle guide member is sized, particularly with respect to its diameter, so as to be insertable into the lumen of a host blood vessel through an arteriotomy. The needle guide member is inserted into the lumen of a host vessel through the arteriotomy, and is positioned relative to the edge of the arteriotomy so that a suture needle guided by the needle guide member is placed at a desired location about the arteriotomy, so as to accurately place a suture for performing the anastomosis. In an alternative use, the needle guide member is inserted into the lumen of the host vessel through a second, adjacent arteriotomy and is then positioned relative to the edge of the first arteriotomy where the anastomosis is to be performed.

Other objects, features, and characteristics of the present invention, as well as methods of operation and function of the related elements of structure, and the combination of parts and economies of manufacture, will become more apparent upon consideration of the following detailed description and the appended claims with reference to the accompanying drawings, all of which form a part of this specification.

BRIEF DESCRIPTION OF THE DRAWINGS

FIGS. 11A and 11B are, respectively, a schematic view of the suture needle guide according to a fourth embodiment thereof, inserted into the lumen of a host vessel and a perspective view from above the guide of the fourth embodiment.

DETAILED DESCRIPTION OF THE PREFERRED EMBODIMENTS

In the following detailed description of the present invention, it is emphasized that the embodiments discussed here are exemplary only, and should not be taken as limiting the scope of the invention. In addition, reference to the attached drawings is made for the purpose of illustrating the invention disclosed herein. No particular representation is made as to the scale of the drawings as limiting the scope of the invention claimed herein.

Figure 3:
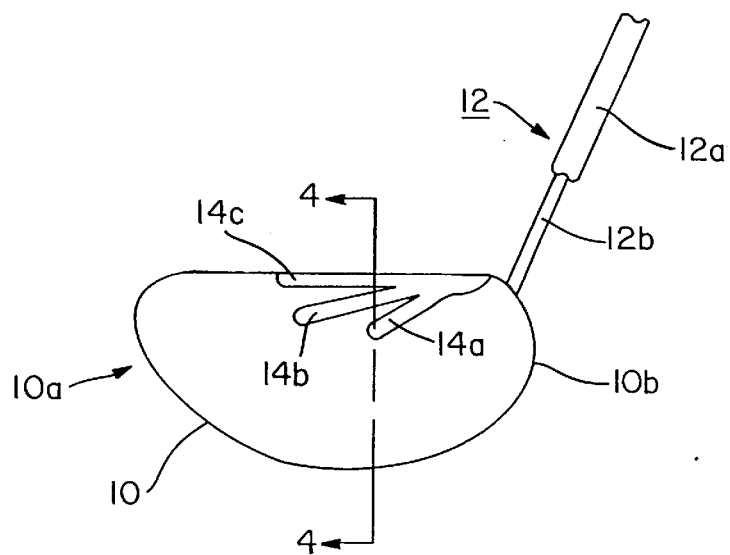
FIG. 3 is a side view of the suture needle guide according to a first embodiment thereof.
Figure 4:
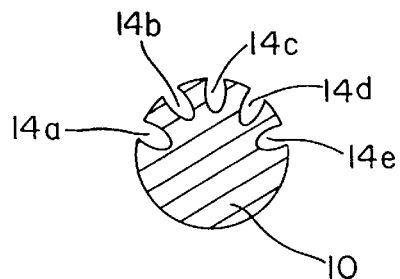
FIG. 4 is a cross-sectional view of the suture needle guide in FIG. 3, taken along line 4—4.
Figure 5:
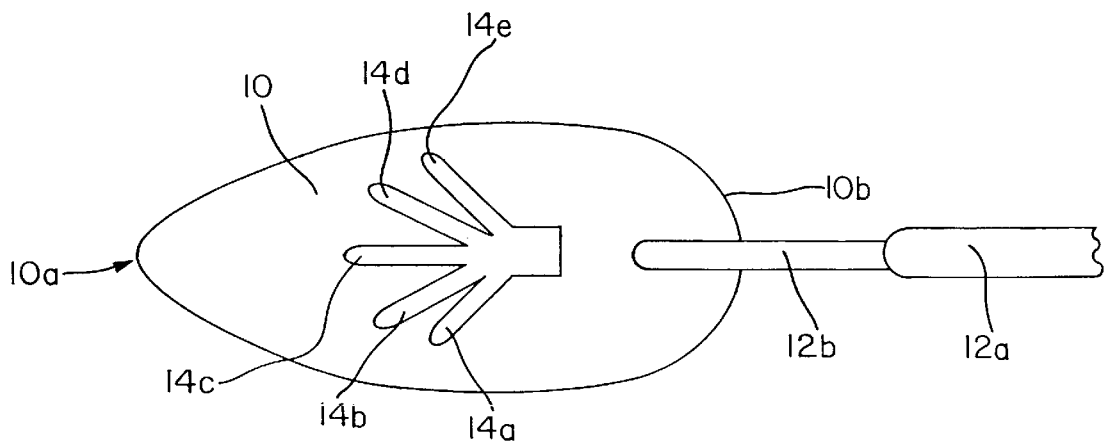
FIG. 5 is a top view of the suture needle guide illustrated in FIGS. 3 and 4.

FIGS. 3–5 illustrate a first embodiment of the present invention. The suture needle guide generally comprises a guide member 10 and a handle 12. The handle 12 may, for example, comprise a handle member 12a and a shaft 12b connecting the handle member 12a and the guide member 10. Shaft 12b may be made slightly flexible in order to increase the ability to sense resistance to movement while inserting and removing the guide member 10 from the lumen. However, shaft 12b may be rigidly connected to guide member 10 and may itself also be flexible to optimize suture guide placement within the host vessel.

The guide member 10 and the handle 12 are preferably made from a material which can be repeatedly sterilized, such as by autoclaving, for example. A suitable example of such a material is stainless steel. In the alternative, the guide member 10 and handle 12 may be disposable, and can therefore be made from a relatively inexpensive material such as plastic or resin, which can be made initially sterile. These considerations apply equally to each of the subsequently described embodiments of the present invention, as well.

Guide member 10 preferably is generally boat-shaped, as seen in FIGS. 3 and 5, having rounded leading end 10a (opposite handle 12) that tapers to a blunt end portion, a trailing end 10b (adjacent handle 12), and generally straight, smooth sides. The rounded or otherwise tapered ends (especially the leading end) of the guide member 10 facilitate insertion and removal from the vascular lumen. The guide member 10 should also preferably have a generally smooth exterior, without abrupt protrusions which could hinder insertion and removal from the lumen. It will be therefore appreciated that guide member 10 may have other shapes suitable to the present invention, such as ellipsoidal.

In general, a portion of the guide member 10 is shaped to guide at least one suture needle, and, preferably, to guide a plurality of suture needles. In the embodiment illustrated in FIGS. 3–5, the peripheral surface of guide member 10 is provided with a plurality of guide grooves or channels 14a, 14b, 14c, 14d, and 14e. In a preferred arrangement, the grooves 14a–14e are arranged so as to diverge from generally the same location on the surface of the guide member 10, as seen in FIGS. 3 and 5. The ends of the diverging grooves are arranged so that they correspond with the circumferential curvature of the edge of an arteriotomy formed in a host vessel. This permits accurate placement of a plurality of suture needles (not shown in FIGS. 3–5) at the periphery of the arteriotomy.

The grooves 14a–14e may be concavely curved to cooperate with curved suture needles. The curvature of grooves 14a–14e preferably matches that of the curved suture needles being used. If curved grooves are provided, it will be appreciated that the respective depths of the grooves, as seen in the cross-sectional view in FIG. 4, preferably will be greater at a midportion thereof than at respective ends.

The grooves 14a–14e are sized in correspondence with the type of suture needle being used therewith, particularly with regard to the length and width of each groove. The width of each groove is preferably such that a respective suture needle can pass freely, but while maintaining a substantially consistent direction of travel in the process of passing the suture needle therealong.

Instead of grooves 14a–14e, it will be appreciated that other needle guiding paths may be provided in the guide member 10. The needle guiding channels formed in the guide member 10 are advantageous because their restricted cross-section helps to further control the motion of a suture needle along the path of a channel (i.e., a suture needle is effectively prevented from moving away from the surface of the guide member 10).

The needles used with the invention may typically be very fine gauge and of a length to facilitate handling such as on the order of ⅓ to 6 inches and may also be flexible stainless steel or even a suitable plastic.

Figure 6:
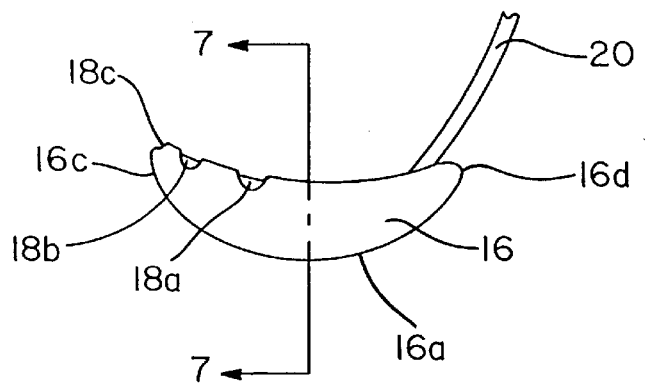
FIG. 6 is a side view of the suture needle guide according to a second embodiment thereof.
Figure 7:
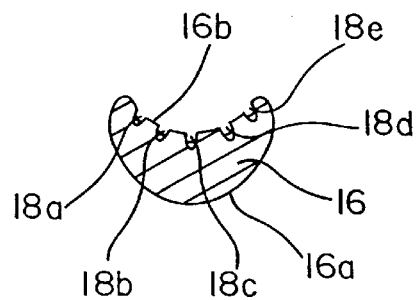
FIG. 7 is a cross-sectional view of the suture needle guide, taken along line 7—7 in FIG. 6.
Figure 8:
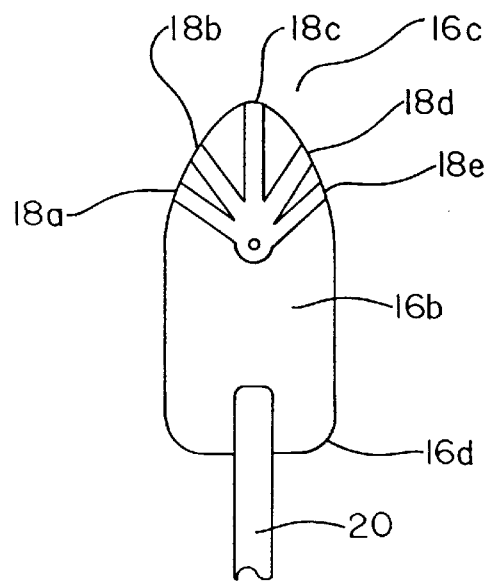
FIG. 8 is a top view of the suture needle guide illustrated in FIGS. 6 and 7.

FIGS. 6–8 illustrate a second embodiment of the present invention. Similar to the first embodiment, the suture needle guide comprises a guide member 16 connected to a handle 20. As mentioned above, the guide member 16 and handle 20 can be made from a material which can be repeated sterilized, or from a relatively inexpensive material which can be initially sterilized and thereafter disposed.

The handle 20 according to this embodiment is constructed with the same considerations described above relative to the first embodiment of the present invention.

Guide member 16 has a hollowed-out, shell-like or canoe-like configuration, including an exterior surface 16a and a generally concave interior surface 16b. Guide member 16 has an overall exterior configuration similar to that of guide member 10 in the first embodiment, namely, a generally smooth body with boat-shaped, rounded, or otherwise tapered leading and trailing ends 16c and 16d, respectively (see FIG. 8, in particular).

Concave interior surface 16b is, in general, shaped to guide at least one, and, preferably, a plurality of suture needles. In the arrangement illustrated here by way of example, interior surface 16b is provided with a plurality of needle guiding grooves or channels 18a–18e. Grooves 18a–18e are preferably arranged in a diverging pattern, wherein they each terminate at a location corresponding to the circumferential curvature of an arteriotomy formed in a host vessel.

Since interior surface 16b is concavely curved, grooves 18a–18e are curved in conformance therewith. The curvature of interior 16b, and, consequently, grooves 18a–18e, preferably corresponds with the curvature of a curved suture needle used in the anastomosis process.

Preferably, grooves 18a–18e extend to the edge of interior surface 16b, as seen, for example, in FIG. 6. This permits a suture needle passed therealong to continue uninterrupted so as to pierce the periphery of the arteriotomy to place a respective suture.

Figure 9:
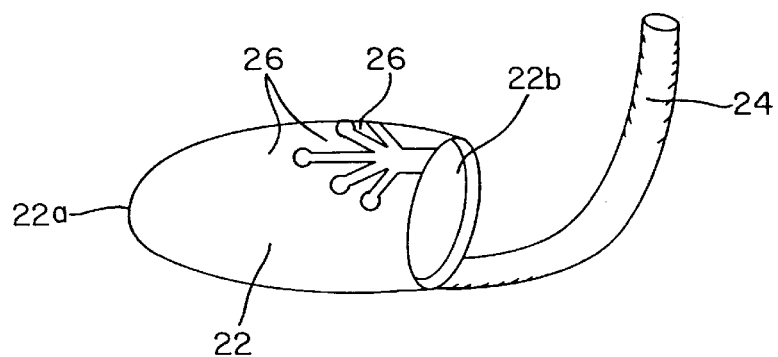
FIG. 9 is a side view of a suture needle guide according to a third embodiment thereof.
Figure 10:
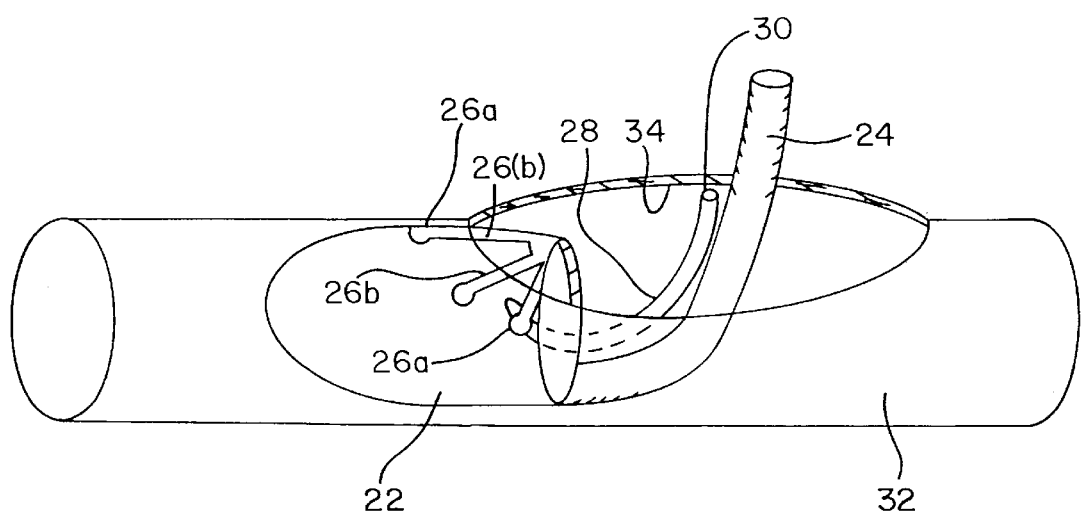
FIG. 10 is schematic view of the suture needle guide according to the third embodiment disposed within the lumen of a host vessel.

FIGS. 9 and 10 illustrate a third embodiment of the present invention. The present invention according to the third embodiment generally comprises a guide member 22 connected to a handle 24. Guide member 22 has a boat-shaped, rounded, or otherwise tapered leading end 22a. Guide member 22 also has a hollow interior, which is open to an exterior via open trailing end 22b. As mentioned above, the guide member 22 and handle 24 can be made from a material which can be repeated sterilized, or from a relatively inexpensive material which can be initially sterilized and thereafter disposed.

The handle 24 according to this embodiment is constructed with generally the same considerations described above relative to the first embodiment of the present invention.

The periphery of guide member 22 is provided with a pattern of openings 26a. Openings 26a are preferably arranged along an imaginary curve coinciding with a periphery of an arteriotomy formed in a host vessel. Openings 26a are sized so as to freely permit respective suture needles to pass therethrough while offering some guidance as to their point of penetration of the host vessel wall. As illustrated in FIGS. 9 and 10, the openings 26a are preferably interconnected by guide paths 26b, which assist in the disengagement of the threads from the guide member 22 during extraction.

FIG. 10 illustrates guide member 22 inserted into the lumen of a host vessel 32 via an arteriotomy 34 formed in the side of host vessel. In FIG. 10, it can be seen how guide member 22 is positioned so that openings 26a are located adjacent to an edge of the arteriotomy 34. Curved suture needle 28, threaded with suture material 30, is passed from inside the guide through an opening in the guide as shown and then through the host vessel wall at the selected site on periphery of the arteriotomy.

A fourth embodiment of the present invention is illustrated in FIGS. 11A–11B. According to this embodiment, a guide member 36 is provided at the end of a handle 38. For example, guide member 36 is substantially contiguous with handle 38, as illustrated. In the illustrated example of the fourth embodiment, handle 38 is a long thin member made from, for example, a slightly flexible material. Handle 38 is preferably flexible in order to allow a surgeon to manipulate guide member 36 at the end thereof within the lumen 40 of host vessel 42. At least a portion of the handle 38 adjacent to guide member 36 has a diameter suitable for insertion into the lumen 40, as seen in FIG. 11A.

Guide member 36 is provided with a surface 44 which is shaped to guide at least one suture needle 46 (threaded with suture material 45). Guiding surface 44 is, for example, curved in accordance with a curvature of suture needles 46.

A periphery of the guiding surface 44 is at least partially surrounded by a portion of flexible material 50. Material portion 50 is arranged relative to guiding surface 44 and the exterior surface of member 36 so that it conforms to the surface contours of guide member 36, substantially without protruding in radial directions. Material portion 50 thus defines a "lip" extending at least part way around the edge of guiding surface 44. Material portion 50 preferably is made from a material which is slightly resistant to being pierced by suture needles 46.

In the previously described embodiments of the present invention, the suture needle guide is first loaded with a sheaf of first needles 46 with the points thereof remaining positioned in the guide 36. According to a preferred embodiment, each first needle 46 is attached to a respective first end of a suture material; each second needle (not shown) is attached to a respective second end of the suture material. The guide 36 is then inserted into the vascular lumen via an arteriotomy and is positioned relative to a periphery of the arteriotomy.

In the instant embodiment, with a plurality of first suture needles 46 prepositioned on the guiding surface 44, before the collective assembly is inserted into the lumen 40 of the host vessel 42, positioning of the points before expression from the guide 36 can be easily accomplished. After suitably positioning the guide with the first suture needles 46, the user will exert force on the rear ends of the first suture needles 46 by, for example, pushing on the sheaf end.

The suture needle guide of this invention is generally used, in performing vascular anastomosis for example, as follows.

The guide member is inserted into the lumen of the host blood vessel through an arteriotomy. An edge of the needle guiding portion of the guide member is aligned with an edge of the opening formed in the host blood vessel.

In the invention according to the first and second embodiments, first suture needles 46 connected to respective first ends of suture material are passed along the respective guide grooves so as to pierce the host blood vessel at the periphery of an opening. Each first suture needle 46 is then drawn therethrough to pull the suture material through the host blood vessel wall. It can be clearly understood that the diverging pattern of guide grooves, channels, or the like, permits a plurality of (for example, five) sutures to be placed about approximately one-half of the periphery of the opening formed in the host blood vessel.

Figure 1:
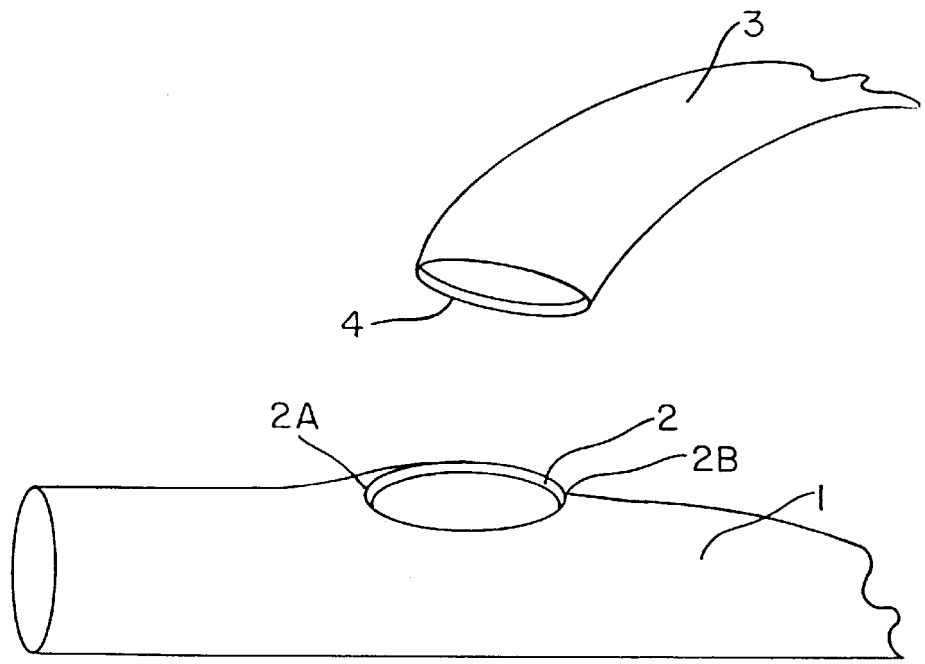
FIG. 1 is a schematic diagram of a host blood vessel and a graft vessel end.
Figure 2:
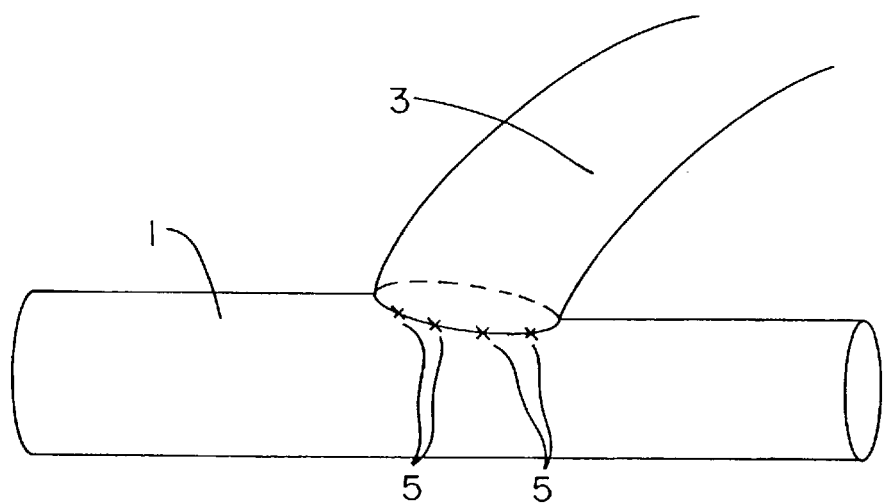
FIG. 2 is a schematic diagram, generally illustrating the anastomotic joining of the host vessel and the graft vessel according to a prior art technique.

Thereafter, each second suture needles (attached to respective second ends of the suture material) is passed through an end peripheral portion of a graft vessel (preferably from the inside to the outside thereof), and the suture material is drawn therethrough as well. Two free ends of the suture material are obtained, by cutting the first and second suture needles from the suture material, for example. The free ends are then temporarily secured together in a known manner, without pulling the respective sutures tight yet. After the sutures at the toe 2a (FIG. 1) of the arteriotomy are completed, the guide member is withdrawn by way of the handle and reinserted into the lumen of the host blood vessel in the opposite direction, and the above-described steps are repeated at the heel 2b of the arteriotomy to form a plurality of sutures about the opening in the host blood vessel.

Finally, the guide member is again withdrawn, and each of the sutures are tightened and tied down, thereby drawing the free end of the graft vessel into substantially sealed communication with the opening formed in the side of the host blood vessel.

As described above, the third embodiment of the present invention, where the guide member is hollow, is also inserted into the lumen of the host blood vessel, as seen in FIG. 10, for example. However, a first suture needle 28, having a first end of suture material 30 connected thereto, first is passed from the interior of the guide outwardly through a guide opening to pierce the host blood vessel at a location corresponding to one of the openings 26 in guide member 22. Before subsequently piercing the end peripheral portion of the graft blood vessel with a second suture needle (not shown) connected to a second end of the suture material, the guide member 22 is withdrawn from the lumen while the trailing end of suture material 30 is grasped or otherwise held in place. This pulls the suture material 30 through a respective opening 26. When a plurality of sutures, corresponding to a plurality of openings 26, are placed, it will be appreciated that the plurality of first suture needles should be passed through the periphery of the opening in the host blood vessel before the guide member 22 is withdrawn from the lumen. The remaining steps are similar to those ōdescribed relative to the first and second embodiments, taking into account the foregoing. For example, the second suture needles (attached to respective second ends of the suture material) preferably are passed through an end peripheral portion of the graft vessel, preferably from the inside to the outside thereof, and the suture material is drawn therethrough.

Use of the fourth embodiment is similar to that of the first, second and third embodiments. However, as previously mentioned, one or more suture needles having suture material connected thereto are prepositioned in the guide member before the guide member is inserted into the lumen of the host blood vessel, through the opening formed therein.

It will also be appreciated that the suture needles which are preferably pointed at each end and suitably curved may be passed through the graft blood vessel end portion first, subsequently positioned in the needle guide, and thereafter passed through periphery of the opening in the host blood vessel.

In an alternative method of use, the suture needle guide may be introduced through a second opening in the host blood vessel which is adjacent to the opening where the anastomosis is performed. After the anastomosis is complete, the second opening is closed in a known manner.

While the invention has been described in connection with what is presently considered to be the most practical and preferable embodiments, it is to be understood that the invention is certainly not limited to these disclosed embodiments, but, on the contrary, is intended to cover various modifications and equivalent arrangements included within the spirit and scope of the appended claims.

What I claim is:

1. A suture needle guide comprising a member and a handle connected to said member, said member having a diameter suitable for insertion into a lumen of a blood vessel and being provided with a portion shaped to guide a suture needle along a path defined by said portion, said member having an upper surface and said at least one groove being concavely curved relative to said upper surface and shaped to guide a correspondingly curved suture needle.

2. The suture needle guide according to claim 1, wherein said member has an exterior surface and said portion is at least one groove shaped to guide a respective suture needle.

3. The suture needle guide according to claim 2, wherein said member has a substantially round cross-section.

4. The suture needle guide according to claim 2, wherein said handle is connected adjacent to an end of said member.

5. The suture needle guide according to claim 1, wherein said portion is a plurality of grooves diverging from a point adjacent to said handle.

6. The suture needle guide according to claim 1, wherein said portion comprises a concavity provided on an exterior surface of said member.

7. A suture needle guide comprising a member and a handle connected to said member, said member having a diameter suitable for insertion into a lumen of a blood vessel and being provided with a portion shape to guide a suture needle along a path defined by said portion, said member having an exterior surface and said portion being at least one groove shaped to guide a respective suture needle, said portion including a plurality of grooves diverging from a point adjacent to said handle.

\* \* \* \* \*